(12) United States Patent
Culbertson et al.

(10) Patent No.: US 6,235,901 B1
(45) Date of Patent: May 22, 2001

(54) OXAZOLINE OR OXAZINE ACETOACETATE AQUEOUS COATING COMPOSITIONS

(75) Inventors: Bill M. Culbertson, Franklin County, OH (US); David L. Trumbo, Racine, WI (US)

(73) Assignee: S. C. Johnson Commercial Markets, Inc.

( * ) Notice: Subject to any disclaimer, the term of this patent is extended or adjusted under 35 U.S.C. 154(b) by 0 days.

(21) Appl. No.: 09/306,302

(22) Filed: May 6, 1999

(51) Int. Cl.$^7$ ................................. C07D 265/08

(52) U.S. Cl. .................. 544/88; 544/96; 544/97; 548/229; 548/237; 548/238

(58) Field of Search ................ 544/88, 96, 97; 548/229, 237, 238

(56) References Cited

U.S. PATENT DOCUMENTS

| | | | |
|---|---|---|---|
| 3,304,328 | 2/1967 | Pelley | 260/562 |
| 3,758,629 | 9/1973 | Thill | 260/80.8 |
| 4,247,671 | 1/1981 | Reitz et al. | 526/260 |
| 4,430,491 | 2/1984 | Culbertson et al. | 528/153 |
| 4,600,766 | 7/1986 | Arita et al. | 528/207 |

OTHER PUBLICATIONS

Monzer, et al., "Reaction Behaviour of Monomeric β–Ketoesters", Macroakron'94, 35$^{th}$ IUPAC International Symposium on Macromolecules, Jul. 11–15, 1994, pp. 1–18 (1994).
Hussain, et al., "Reactions of Acetoacetanilides—A Century of", J. Heterocyclic Chem., 25 9–22 (1998).
Wacker Chemicals (USA), Inc. literature, pp. 1–12 (admitted prior art).
Clemens, et al., "Acetoacetoxyethyl Methacrylate (AAEM) Acetoacetyl Chemistry", For the Resins Market—Eastman Chemical Products, Inc. Communication, pp. 1–12 (1995).
Edgar, et al., "Synthesis and Properties of Cellulose Acetoacetates", Macromolecules 1995, 28, 4122–4128 (1995).
Sato, et al., "Synthesis of copper(II) chelate of ethyl α–(acetoacetoxy–methyl)acrylate and its radical–Initiated polymerization", Makromol. Chem. Rapid Commun. 11, 553–557 (1990).
Ran, et al., "Polymer–Supported Lewis Acid Catalysts. V. Complexes of Titanium Chloride or Stannic Chloride with Poly(β–Diketone) Carrier", J. Macromol. Sci.—Chem., A27(5), pp. 625–636 (1990).
D.L. Trumbo, "Michael Addition Polymers from Bisacetoacetates", Polymer Bulletin 26, 481–485 (1991).
Grawe, et al., "Chelation As a Means of Developing Crosslinking Emulsions", J. Coatings Technology, vol. 52, No. 661, pp. 73–87 (1980).
Kobayashi, et al., Encyclopedia of Polymer Science and Engineering, vol. 4, pp. 525–537 (1986).

Odian, et al., "Zwitterion Polymerization of Tetrahydro–1–[4–hydroxy–3–(2–hydroxyethoxy)phenyl] Thiophenium Hydroxide Inner Salt", Macromolecules, 23(4), 918–925 (1990).
C.I. Simionescu, et al., "Spontaneous Copolymerization of 2–methyl–2–oxazoline and N–phenylmaleimide" Abstract from Polymer Bulletin (1985).
T. Saegusa, "Sequence Regulation in Spontaneous Binary and Ternary Copolymerizations via Zwitterion Intermediates", Makromol. Chem., Suppl. 4, 73–84 (1981).
Rivas, et al., "Copolymerization via Zwitterion of 2,4, 4–trimethyl–2–oxazoline with N–phenylmaleimide and p–methoxyphenylmaleimide", Eur. Polym. J., 25(10), 1001–1005 (1989).
Canessa, et al., "Copolymerization via Zwitterion", Abstract from Polym. Bull. (Berlin) (1984).

(List continued on next page.)

*Primary Examiner*—Richard L. Raymond
(74) *Attorney, Agent, or Firm*—Renee J. Rymarz; Neil E. Hamilton; Warren R. Bovee

(57) ABSTRACT

A novel compound having the formula:

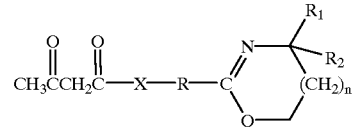

wherein R is an alkyl group containing 1–5 carbon atoms or an aryl, substituted aryl, substituted or unsubstituted heteroaryl, alkyl-aryl, alkylether-aryl or O; $R_1$ and $R_2$ are hydrogen or a methyl group; X is O, NH, NR' wherein R' is an alkyl group containing 1–5 carbon atoms, or O—R" or NR" wherein O—R" is O-alkyl-O or O-alkyl, NR" is O-alkyl-ONH,

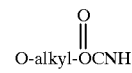

wherein each instance alkyl contains 1–5 carbon atoms and n is 0 or 1.

The compound of this invention is useful as a monomer which can be polymerized and/or copolymerized by catonic polymerization.

Polymers and copolymers produced in this invention can be crosslinked and are useful in coatings, inks, overprint varnishes, and surface treatment applications.

20 Claims, No Drawings

OTHER PUBLICATIONS

Nishikubo, et al., "Novel Synthesis of alternating copolymers with amide and thioether linkages by polyaddition reactions of bifunctional cyclic iminoethers with dithiols", Mackromol. Chem., 185, 1307–1316 (1984).

Kagiya, et al., "Preparation of a crystalline poly(ester–amide) by the polyaddition reaction of bisoxazoline and a dicarboxylic acid", Polymer Letters, 4, 257–260 (1966).

J.A. Frump, "Oxazolines: Their preparation, reactions, and applications", Chem. Rev., 71(5), 483–505 (1971).

Culbertson, et al., "Thermosetting Marix Compositions with improved toughness to meet new FAA aircraft interiors fire worthiness requirements", SAMPE Symp., Mar. 7–10, pp. 1531–1545 (1988).

Culbertson, et al., "Bisoxazoline–phenolic resin step–growth copolymerizations: new systems for Electronic, mold making, and resin transfer molding", SAMPE Symp., May 8–11, pp. 2483–2497 (1989).

Kobayashi, et al., "Novel Multifunctional initiators for Polymerization of 2–Oxazolines", Macromolecules, 25(12), 3232–3236 (1992).

Witte, et al., "Cyclische Imidsäureester aus Nitrilen und Aminoalkoholen", Liebigs Ann. Chem. 996–1009, (1974).

Rasoul, et al., "Oxazoline Hydrolysis, Synthesis and Polymerization of a New Oxazoline Methacrylate", Polymer Preprints, ACS, pp. 871–872, (1997).

OXAZOLINE OR OXAZINE ACETOACETATE AQUEOUS COATING COMPOSITIONS

CROSS-REFERENCE TO RELATED APPLICATIONS

None

STATEMENT REGARDING FEDERALLY SPONSORED RESEARCH OR DEVELOPMENT

None

BACKGROUND OF THE INVENTION

1. Technical Field

This invention relates to an aqueous coating composition such as coatings, inks, coverprint varnish and surface treatment applications containing an oxazoline or oxazine acetoacetate polymer.

2. Background Art

In the following description of the prior art and in the Examples, the parenthetical numbers are described in the following Reference section. Acetoacetamide, acetoacetanilide, and acetoacetate functionalized chemicals are readily available, via reaction of amines or hydroxyl substituted molecules with diketene (1–3), alkyl acetoacetates, or the readily used acetoacetalation compound 2,2,6-trimethyl-1,3-dioxin-4-one, which is prepared from reaction of diketene with acetone (2,4). Organic compounds or polymers with the acetoacetamide, acetoacetanilide, or acetoacetate type functionality are known to react with a variety of other functional chemicals (1–5), including such things as amines, aldehydes, and isocyanates, giving various adducts in excellent yields at low reaction temperatures (2). Also, the acetoacetamide, acetoacetanilide, or acetoacetate group, with amine catalysts, will combine readily with the acrylate functionality, via what is commonly called the Michael addition reaction (2,5,6). Further, these acetoacetanilide, acetoacetamide, or acetoacetate groups are known to readily react with various metal compounds, such as CaO, Ca(OH)$_2$, BaO, CoCl$_2$, NiCl$_2$, etc. to form metal complexes (1,3), where the chemistry has been used to prepare polymeric catalysts (2,7,8) and crosslinked coatings (6,9–11). These chemicals with the acetoacetamide, acetoacetanilide, and/or acetoacetate functionality, which have three active centers, have found extensive utility in the formation of metal-complexes, manufacture of dyes and synthesis of heterocycles (1–3).

It is well known that cyclic imino ethers, such as oxazolines and oxazines will undergo cationic, ring-opening polymerizations (12) and zwitterionic copolymerization with such things as acrylic acid, maleimides, anhydrides, lactones, etc. (13–17). It is also well known that molecules with the oxazoline or oxazine residues will undergo ring-opening reactions with compounds such as carboxylic acids, thiols (HS-groups), phenols, alkyl halides, etc., giving 1-to-1 adducts (18–24), allowing for step-growth copolymerizations to be readily achieved with difunctional monomers. Further, it has been shown that alkyl halides will initiate ring-opening polymerization of cyclic imino ethers, as well as give 1:1 adducts (18, 25). Thus oxazolines and oxazines are excellent intermediates for synthesis of variety of polymeric materials, both thermoplastics and thermosets, by chain-growth and step-growth polymerization mechanisms or combinations thereof. In addition, the synthesis and polymerization of oxazoline and oxazine methacrylate aqueous coating compositions are also known (27).

REFERENCES

1. U.S. Pat. No. 3,304,328 (Feb 14, 1967) to FMC Corporation.
2. N.Moszner, U.Salz, V. Rheinberger, MACROAKRON '94, 35th IUPAC Int. Symp. on Macromolecules, Jul. 11–15, 1994 paper.
3. S. M. Hussain, A. M. El-Reedy, S. A. El-Sherabasy, J. Heterocyclic Chem., 25, 9–22 (1988).
4. Wacker Chemicals (USA), Inc. literature, p. 16.
5. R. J. Clemens, J. S. Witzman, F. Del Rector, Communications of Eastman Chemical Products, Inc.
6. K. J. Edgar, K. M. Arnold, W. W. Blount, J. E. Lawniczak, and D. W. Lowman, Macromolecules 1995, 28, 4122–4128.
7. T.Sato, A. Morita, I. Kamiya, T. Ota, Makromol. Chem., Rapid Comm.11 (1990) 553.
8. R.Ran, D.Fu, J. Macromol.Sci.-Chem.A27 (1990) 625.
9. D. L. Trumbo, Polymer Bull.26 (1991) 265,481.
10. J. R. Grawe, B. G. Burkin, J. Coatings Technol. 52 (1980) 73.
11. U.S. Pat. No. 4,247,671 (Jan. 27, 1981) to Rohm and Haas Co.
12. S.Kobayashi and T. Saegusa, Encyclopedia of Polymer Science and Engineering, Wiley & Sons, New York, Vol. 4, pp. 525–537, 1986.
13. G. Odian, M.P. O'Callaghan, C. K. Chien, P. Gunatillake, M. Periyasay and D. L. Schmidt, Macromolecules, 23(4), 918–927 (1990).
14. C. I. Simionescu, et.al., Polymer.Bull. (Berlin), 14(1), 79–83 (1985).
15. T. Saegusa, Makromol. Chem., Suppl., 4, 73–84 (1981).
16. B. L. Rivas and G. D. Pizarro, Eur. Polym. J., 25(10), 1001–1005 (1989).
17. G. S. Canessa, A. S. Pooley, M.Parra and B. L. Rivas, Polym. Bull.(Berlin), 11(5), 465–70 (1984).
18. J. A. Frump, Chem.Rev., 71(5), 483–505 (1971).
19. U.S. Pat. No. 3,758,629 (Sept. 11, 1973), to Dow Chemical.
20. U.S. Pat. No. 4,600,766 (Jul. 15, 1986) to Takeda Chemical Co.
21. T. Nishikubo, T. Iizawa and A. Tokairin, Mackromol. Chem., 185, 1307–1316 (1984).
22. T. Kagiya, S. Narisawa, T. Maeda and K. Fukui, Polymer Letters, 4, 257–260 (1966).
23. U.S. Pat. No. 4,430,491 (Feb. 7, 1984) to Ashland Chemical Co.
24. B. M. Culbertson, M. L. Deviney, 0. Tiba and D. D. Carlos, 33rd SAMPE Symp., March 7–10, pp. 1530–1545 (1988), Ibid. 34h SAMPE Symp. May 8–11, 1989. PP.2483–2497.
25. S. Kobayashi, H. Uyama, Y. Narita and J. Ishiyama, Macromolecules, 25(12), 3232–3236 (1992).
26. H. Witte and W. Seelinger, Liebigs Ann. Chem., 996–1009 (1974).
27. H. A. A. Rasoul, D. B. Obuchowski, D. L. Trumbo, B. M. Culbertson, and Y. Xue, Oxazoline Hydrolysis, Synthesis and Polymerization of a New Oxazoline Methacrylate, PP. 871–872 (1997).

The prior art fails to disclose chemical compositions, monomeric or polymeric having both the cyclic imino ether and the acetoacetamide, acetoacetenilide or acetoacetate residues on the same molecule.

SUMMARY OF THE INVENTION

The novel compound of this invention has the following formula:

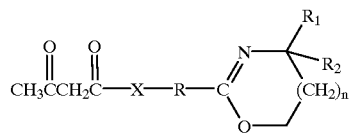

wherein R is an alkyl group containing 1–5 carbon atoms or an aryl, substituted aryl, substituted or unsubstituted heteroaryl, alkyl-aryl, alkylether-aryl or O; $R_1$ and $R_2$ are hydrogen or a methyl group; X is O, NH, NR' wherein R' is an alkyl group containing 1–5 carbon atoms, or O—R" or NR" wherein O—R" is O-alkyl-O or O-alkyl, NR" is O-alkyl-OHN, ) or

wherein each instance alkyl contains 1–5 carbon atoms and n is 0 or 1.

The compounds of this invention are monomers which may be polymerized or opolymerized, via cationic, ring-opening polymerization of the cyclic imino ether residues, producing polymers with pendant acetoacetamide, acetoacetanilide and/or acetoacetate groups. Polymers of the aforesaid type may be readily crosslinked, via a variety of reactions as explained in the background art, to produce crosslinked materials useful in coatings, adhesives, and other applications. Further, these monomers and polymers are shown to readily form metal complexes with a variety of metal salts, giving in many cases, highly colored monomer-metal or macromolecular-metal complexes.

Referring to the previous formula, in the instance where R is aryl, X is NH, $R_1$ and $R_2$ are H and n is 0, this compound can be readily prepared by reacting an aminophenyl oxazoline with diketene. In the instance where R is aryl, X is NH, $R_1$ and $R_2$ are H and n is 1,2-(4-aminophenyl) oxazine was reacted with diketene. The compound where R is aryl, X is NR', $R_1$ and $R_2$ are H and n is 0, this compound is prepared by reacting aminobenzonitrile with an alkyl iodide to obtain an alkylaminobenzonitrile which is treated with ethanolamine to obtain alkylaminophenyl oxazoline. The resulting oxazoline compound is subsequently treated with 2,2,6-trimethyl-1,3-dioxin-4-one (TDO). The compound where R is aryl, X is NH, R, $R_1$ and $R_2$ are $CH_3$ and n is 0 is prepared by reacting ethylaminobenzoate with methylaminopropanol to yield a dimethyl derivative of aminophenyl oxazoline with the resulting oxazaline treated with TDO. The compound where R is alkyl, X is alkyl, $R_1$ and $R_2$ are hydrogen and n is 0 is prepared by reacting an alkylamino alkylnitrile with ethanolamine to obtain alkylamino alkyloxazoline which is subsequently treated with TDO. As to the compound where R, $R_1$, $R_2$ and n are as immediately and previously described but X is O-alkyl, it is obtained by reacting hydroxyalkyl oxazoline and TDO. In those instances where R is aryl, $R_1$ and $R_2$ are hydrogen, n is 0 and X is O-alkyl-O, O-alkyl-CNH or

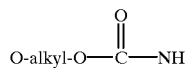

the following procedures were employed. Where X is O-alkyl-O, hydroxy-alkylphenyl oxazoline was reacted with TDO; where X is O-alkyl-CONH aminophenyl oxazoline was reacted with an alkyllactone resulting in a hydroxyalkyl substituted amide of the oxazoline compound which is subsequently treated with TDO; where X is

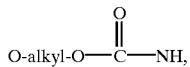

aminophenyl oxazoline was treated with an alkylene carbonate to obtain an intermediate carbamate deriviative which is subsequently treated with diketene.

To synthesize substituted aryl oxazolines, a substituted aminobenzonitrile such as methyl substituted aminobenzonitrile is reacted with 2-aminoethanol in the presence of a zinc acetate catalyst as set forth in Example 1 to provide an amino and methyl substituted phenyloxazoline. The resulting substituted phenylaxazoline is reacted with diketene in the manner of Example 4 to produce the desired substituted aryl oxazoline. As indicated, the substituents on the phenyl group can be alkyl and other functionalties can include nitro and hydroxyl.

To prepare the compounds of general formula where R is heteroaryl, a heterogroup of the formula:

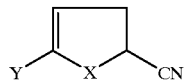

is reacted with 2-aminoethanol as previously described to result in a compound of the formula:

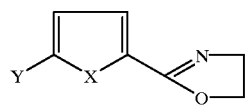

which is subsequently reacted with diketene. In the foregoing formula X=sulfur, oxygen, or NH or NR where R is alkyl and Y=hydrogen, bromine, chlorine, iodine fluorine, amino or hydroxyl.

To prepare compounds of the general formula where R is alkyl-aryl, a compound of the formula:

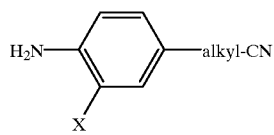

is reacted with 2-aminoethanol as previously described to result in:

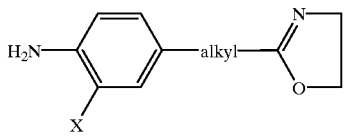

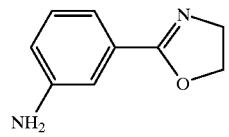

which is subsequently heated with diketene to produce the desired alky-aryl substituted or unsubstituted acetoacetoxazoaline. In this instance X =hydrogen, carboxyl, halogen, alkyl or aryl.

To synthesize compounds of the general formula where R is alkylether-aryl, a hydroxybenzonitrile is reacted with 2-aminoethanol as previously described to result in a hydroxy substituted phenyloxazoline. This intermediate oxazoline is reacted with, for example ethylene oxide, to produce a compound of the formula:

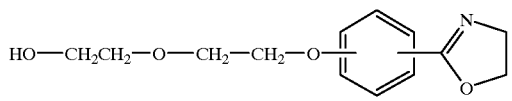

which is further reacted with diketene to produce the desired alkylether-aryl substituted acetoacetate oxazoline.

The term "alkyl" as used herein means an alkyl group having 1–5 carbon atoms.

The Examples which follow are intended as an illustration of certain preferred embodiments of the invention, and no limitation of the invention is implied.

EXAMPLE 1

2-(4-Aminophenyl)oxazoline (4-APOXO)

Using known procedures for the synthesis of cyclic imino ethers from nitriles (18,26), 4-aminobenzonitrile was treated with an excess of 2-aminoethanol (1 part nitrile/2 parts aminoalcohol) in refluxing xylene, with 3.5 wt. % zinc acetate catalyst, with all under a slow nitrogen stream. The solution was heated until no $NH_3$ was detected in the off gas. After removal of the xylene, the crude solid product was obtained in high yield. The crude product was recrystallized from acetonitrile to obtain an 82% yield of white, crystalline 4-APOXO having mp 163–165° C., reported 158–160° C. The structure of the monomer was confirmed by FT-IR and $^1H$ NMR. Structure of 4-APOXO is as follows:

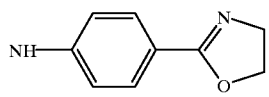

EXAMPLE 2

2-(3-aminophenyl)oxazoline (3-APOXO)

Example 1 procedure was followed starting with 3-aminobenzonitrile in place of the 4-amino compound, providing white, crystalline APOXO isomer in a 75% yield, with mp 126–128° C. FT-IR and $^1H$ NMR confirmed the structure shown below:

EXAMPLE 3

2-(4-aminophenyl)oxazine (4-APOXI)

While this monomer is new to the literature, it is obvious the monomer may be made by published techniques used for Example 1 and 2 compositions. Example 1 procedure was followed, with replacement of the 2-aminoethanol by 3-aminopropanol (3-hydroxypropyl amine) for the oxazine synthesis procedure. The heretofore unreported crystalline 4-APOXI, with mp 177–178° C., was obtained in 92% yield. The structure, shown below, was confirmed by elemental analysis, FT-IR and $^1H$ NMR.

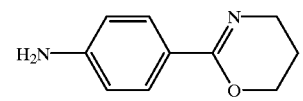

EXAMPLE 4

2-(4-acetoacetanilide)oxazoline (4-AAOXO)

To a stirred solution of 4-APOXO, 20.4 g (0.136 mol), in 280 ml of tetrahydrofuran (THF), contained in a 500 ml round bottom flask fitted with a reflux condenser and $N_2$ sparge tube, was added 10.8 ml (0.14 mol) of diketene in dropwise fashion, keeping the temperature at 0–5° C. After 30 min, the temperature was allowed to rise to room temperature and the flask and contents allowed to sit for several hours. Evaporation of the solvent produced the crude, solid product in essentially quantitative yield. Recrystallization from acetonitrile produced white, crystalline 4-AAOXO with mp 171–172° C. Elemental analysis, FT-IR and $^1H$ NMR confirmed the structure of the heretofore unreported monomer, as shown below:

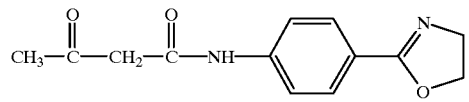

EXAMPLE 5

2-(4-acetoacetanilide)oxazoline (4-AAOXO)

This Example illustrates an alternative synthesis of the above compound. 4-APOXO was reacted with t-butyl acetoacetate to yield 4-AAOXO in excess of 85% acording to the following reaction conditions: 30 g of 4-APOXO were charged to a 500 ml round bottom flask equipped with a mechanical stirrer, thermometer, Dean-Stark trap and reflux condenser. 200 ml of xylene was added followed by 29.3 g of t-butyl acetoacetate. The reaction mixture was heated with stirring to 105° C. The rapid evolution of t-butanol began at this point and continued for 15–20 minutes. The solvent was removed under reduced pressure and the solid residue of the desired product was recrystallized twice from acetonitrile and had a m.p. 170–171° C.

EXAMPLE 6

2-(4-acetoacetanilide)oxazoline (4-AAOXO)

This is a duplication of Example 4, except using different starting material. A 250 ml three-neck, round bottom flask was fitted with a nitrogen gas inlet tube, magnetic stirrer, thermometer, and condenser. 4-APOXO, 8.0 g (54 mmol), was mixed with 2,2,6-trimethyl-1,3-dioxin-4-one (TDO), 8.0 ml (61 mmol), and 120 ml of xylene. The solution was heated at reflux, under a slow nitrogen stream, for 4 hrs. On cooling, the crude 4-AAOXO precipitated from solution. The 4-AAOXO was collected, washed with diethyl ether, and dried in a vacuum to obtain the slightly yellow, crystalline monomer in 83% yield, having mp 169–171° C. FT-IR and $^1$H NMR confirmed the product to be the same as that prepared in Example 4.

EXAMPLE 7

2-(3-acetoacetanilide)oxazoline (3-AAOXO)

Using Example 4 procedure, 3-APOXO was treated with a slight excess of diketene to produce 3-AAOXO in 65% yield, with the recrystallized waxy solid having mp 77–78° C. Elemental, FT-IR and $^1$H NMR confirmed the 3-AAOXO structure, as shown below:

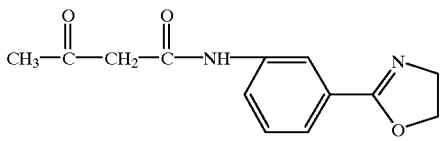

EXAMPLE 8

2-(4-acetoacetanilide)oxazine (4-AAOXI)

Using Example 4 procedure, 4-APOXI was treated with a slight excess of diketene to produce crude 4-AAOXI in essentially quantitative yield. Recrystallizion from acetonitrile gave the new monomer in 88% yield, having mp 133–134° C. The structure, shown below, was confirmed by elemental analysis, FT-IR and $^1$H NMR spectroscopy.

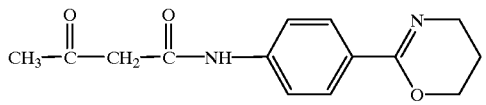

EXAMPLE 9

N-Methyl-N-[4-(2-oxazolin-2-yl)phenyl]acetoacetamide

This compound was prepared by treating 4-aminobenzonitrile with a slight excess, on a molar equivalents basis, of methyl iodide in tetrahydrofuran solvent for 4 hrs at room temperature. Removal of the THF and other volatiles, followed by recrystallization, gave a 76% yield of 4-(N-methyl)aminobenzonitrile, mp 85–87° C. Using Example 1 procedure, the aforesaid substituted nitrile was treated with ethanolamine to obtain a 70% yield of 2-[4-(N-methyl) aminophenyl]oxazoline, mp 145–147° C. Following the Example 6 procedure, the aforesaid compound was treated with TDO to form the oxazoline shown below, having a methyl group attached to the nitrogen in the acetoacetanilide segment. The product was recrystallized from ethyl acetate, mp 102–105° C. Elemental analysis, FT-IR, exhibiting 1726 (C—O) and 1635 (—C═N—) cm$^{-1}$ absorptions, and with $^1$H NMR confirmed the below drawn structure.

This compound has the following structure:

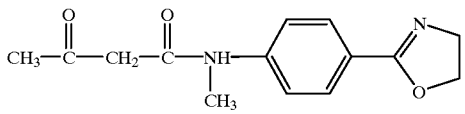

EXAMPLE 10

N-[4-(4,4-dimethyl-2-oxazolin-2-yl)phenyl]acetoacetamide

Ethyl p-aminobenzoate, 20.65 g (0.125 mol), 2-methyl-2-aminopropanol, 22.3 g (0.25 mol) 150 ml of xylene, and 0.25 g of lithium amide were combined and heated at the reflux temperature for 50 hr. The alcohol and water liberated was collected in a Dean-Stark trap, providing indication when the reaction was complete. The xylene solvent was removed and the viscous liquid was added to water to precipitate the product. After drying, a 15.5 g (65%) yield of the 4,4-dimethyl derivative of 4-aminophenyl oxazoline was obtained. The product was recrystallized from ethyl acetate, giving white, crystalline material with mp 172° C. FT-IR, with peaks centered at 3445 (NH), 1635 (—C═N—), and 1602 (phenyl) cm$^{-1}$ confirmed the desired amino functionalized oxazoline. Following the Example 6 procedure, TDO was used to covert the aforesaid compound to the desired acetoacetamide. The structure of this new composition is as follows:

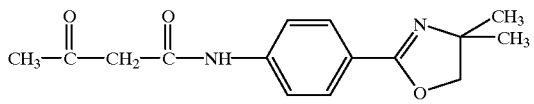

EXAMPLE 11

N-Methyl-N-[2-(2-oxazolin-2-yl)ethyl]acetoacetamide

3-Methylaminopropionitrile, 50 g (0.59 mol), ethanolamine, 73.2 g (1.2 mol), 3.2 g of zinc acetate, and 100 ml xylene were combined and heated at reflux under nitrogen. When no more NH$_3$ was detected coming from the reaction, the xylene was removed and the crude product purified by distillation, bp 80–82° C./45 mm Hg. The FT-IR, of the slightly yellow colored liquid, showed a broad NH peak at 3370 cm$^{-1}$, and the expected —C═N-peak at 1637 cm$^{-1}$, supporting preparation of the desired intermediate 2-[2-(N-methyl-amino) ethyl] oxazoline. Using the Example 6 procedure, the aforesaid intermediate was treated with a slight molar excess of TDO in xylene solvent, obtaining the desired N-methyl-N-[2-(2-oxazolin-2-yl)ethyl] acetoacetamide as a yellow colored liquid. The FT-IR, with peaks centered at 3304, 2941, 1718, and 1649 cm$^{-1}$, and $^1$H NMR spectra supported the following structure.

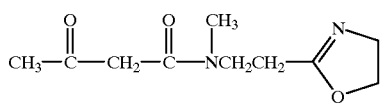

EXAMPLE 12

Acetylacetonate Derivative of 2-(3-Hydroxypropyl) oxazoline

The compound 3-hydroxypropyl-2-oxazoline was prepared by techniques known in the patent (11) literature. A reaction flask was charged with 10.6 g (0.5mol) of 3-hydroxypropyl-2-oxazoline, 11.4 g (0.08 mol) of TDO, and 100 ml of xylene. Heating with stirring under nitrogen at the reflux temperature of xylene for 6 hr. followed by removal of volatiles, gave a viscous oil. The FT-IR and $^1$H NMR spectra were supportive of the following structure,

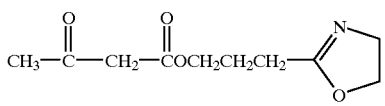

EXAMPLE 13

Acetylacetonate Derivative of 2-(3-Hydroxypentyl) oxazoline

Using the technique outlined in Example 12, 2-(5-hydroxypentyl) oxazoline was prepared and treated with excess TDO to obtain a good yield of the desired acetylacetonate derivative shown below. The FT-IR and $^1$H NMR confirmed the following structure.

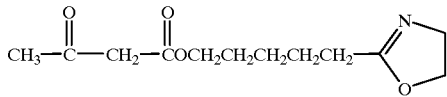

EXAMPLE 14

Acetylacetonate Derivative of 2-(p-Hydroxyethoxyphenyloxazoline)

A 250 ml. round bottom, three-neck flask was charged with 2-(p-hydroxyethoxyphenyl) oxazoline, 8.28g (0.04 mol TDO, 11.36g(0.08 mol) and 120 ml of xylene. The solution was stirred and heated at reflux, under nitrogen, for 5 hr. Evaporation of the solvent gave a high yield of the crude, solid product. After washing with ethyl acetate, the product was recrystalized from petroleum ether to give a good yield of the desired compound, mp 72–75° C. Elemental analysis, FT-IR and $^1$H NMR spectra supported the structure shown below.

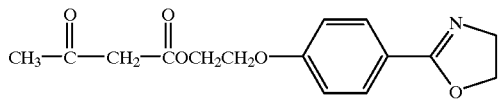

EXAMPLE 15

Acetylacetate Derivative of the Butyrolactamide

The monomer 2-(4-aminophenyl)oxazoline was combined and heated under nitrogen with a slight excess of butyrolactone, giving an excellent yield of the desired hydroxyalkyl substituted amide of the starting aminophenyl oxazoline compound. The latter composition was treated with an excess of TDO to obtain the compound with the following structure in excellent yield, with structure confirmed by FT-IR and $^1$H NMR spectroscopy.

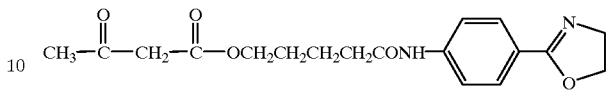

EXAMPLE 16

Acetoacetate Derivative of the Hydroxyethyl carbamate prepared from 2-(4-Aminophenyl) oxazoline 4-APOXO was treated with a slight molar excess of ethylene carbonate to prepare the following carbamate, as shown:

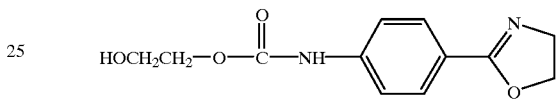

The above compound, which is unknown to the literature, was treated with a slight excess of diketene, per Example 4, to prepare in excellent yield the desired acetoacetate monomer, with structure shown below confirmed by FT-IR and $^1$H NMR spectroscopy.

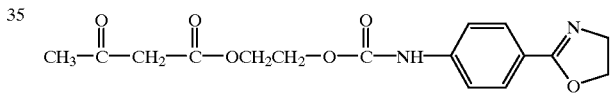

EXAMPLE 17

Polymerization of 2-(4-acetoacetanilide)oxazoline (4-AAOXO)

The monomer 4-AAOXO, 4.0 g, and anisole (50 ml) solvent, along with a catalytic amount (0.15 g.) of the cationic polymerization initiator, methyl tosylate (TsOCH$_3$), were combined under nitrogen and sealed in a small reaction flask containing a magnetic stir bar. With stirring, the polymerization was run for 10 hr at 135° C. After cooling, the anisole solution was combined with hexane to precipitate the polymer. After collection and drying under vacuum at 45° C., the poly (4-AAOXO), soluble with difficulty in N,N-dimethylformamide (DMF), was obtained in essentially quantitative yield. The polymer structure was confirmed by FT-IR and is $^1$H NMR analysis. Polymerization under the same procedure with acetonitrile solvent and SnCl$_4$ initiator produced poly (4-AAOXO) which was readily soluble in DMF.

EXAMPLE 18

Copolymerization of 2-(4-acetoacetanilide) oxazoline (4-AAOXO) with 2-phenyloxazoline The monomer 2-(4-acetoacetanilide) oxazoline [4-AAOXO], 2.5 g. and 2-phenyloxazoline (2.5 g.), with 0.15 g of TsOCH₃ were mixed in a small glass vial containing 45 ml of anisole. The vial was flushed with nitrogen, sealed, and placed in a thermostatted bath at 120° C. for 13 hr. The polymer solution, after cooling, was combined with vigorously stirred petroleum ether to precipitate the copolymer. The copolymer was collected, washed with petroleum ether, and dried under vacuum at 45° C. FT-IR and $^1$H NMR spectra confirmed the copolymer contained both monomer residues.

EXAMPLE 19

Copolymerization of 4-AAOXO with Ethyl Oxazoline

Using the procedure described in Example 18, a copolymer of 4-AAOXO and 2-ethyloxazoline was produced and isolated in high yield. FT-IR and $^1$H NMR confirmed that the copolymer contained both monomer residues.

EXAMPLE 20

Copolymerization of 3-AAOXO with 2-phenyloxazoline

Using Example 18 procedure, the copolymer of 3-AAOXO and 2-phenyloxazoline was obtained in high yield. FT-IR confirmed that the copolymer contained both monomer residues.

The desired molecular weights for the copolymers of Examples 19 and 20 are in the range of 6,000–25,000.

EXAMPLE 21

Copolymerization of 4-AAOXI with 2-phenyloxazoline

Using Example 18 procedure, the copolymer of 4-AAOXI and 2-phenyloxazoline was obtained in high yield. FT-IR and $^1$H NMR confirmed that the copolymer contained both monomer residues.

While Example 19 illustrates the copolymerization of 4-AAOXO with ethyl oxazoline, it is obvious that the corresponding oxazine compounds could be employed.

EXAMPLE 22

Formulation

Aqueous formulations of the compounds of this invention can be produced by copolymerizing the compounds with ethyl oxazoline. Specifically the ethyl oxazoline should be present in an amount of 90 mole percent. When 4-AAOXO was employed, these solutions can be mixed with a crosslinker and drawn down over any substrate.

Industrial Applicability

The monomers of this invention when further crosslinked at room temperature result in polymers useful in coatings, inks, overprint varnishes, and surface treatment applications.

That which is claimed is:
1. A compound having the formula:

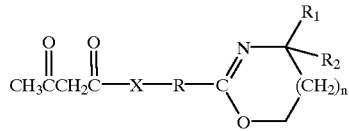

wherein R is an alkylene group containing 1–5 carbon atoms or an arylene, substituted arylene, substituted or unsubstituted heteroarylene, alkylenearylene, alkylene-O-arylene or O; $R_1$ and $R_2$ are hydrogen or a methyl group; X is O, NH, NR' wherein R' is an alkyl group containing 1–5 carbon atoms, or
—O-alkylene-O—, —O-alkylene-, —O-alkylene-ONH- and —O-alkylene-OC(O)NH— wherein each instance contains 1–5 carbon atoms and n is 0 or 1.

2. The compound of claim 1 wherein R is arylene, X is NH, NR or NR', $R_1$ and $R_2$ are hydrogen or a methyl group and n is 0 or 1.

3. The compound of claim 1 wherein R is arylene, X is NH, $R_1$ and $R_2$ are hydrogen and n is 0.

4. The compound of claim 1 wherein R is arylene, X is NH, $R_1$ and $R_2$ are hydrogen and n is 1.

5. The compound of claim 1 wherein R is arylene, X is NR', $R_1$ and $R_2$ are hydrogen and n is 0.

6. The compound of claim 5 wherein R' is methyl.

7. The compound of claim 1 wherein R is arylene, X is NH, $R_1$ and $R_2$ are $CH_3$ and n is 0.

8. The compound of claim 1 wherein R is an alkylene group, X is NR', $R_1$ and $R_2$ are hydrogen and n is 0.

9. The compound of claim 8 wherein R is ethylene.

10. The compound of claim 8 wherein R' is methyl.

11. The compound of claim 1 wherein R is an alkylene group, X is -O-alkylene-, $R_1$ and $R_2$ are hydrogen and n is 0.

12. The compound of claim 11 wherein —O-alkylene- is —O-propylene-.

13. The compound of claim 11 wherein —O-alkylene- is —O-pentylene-.

14. The compound of claim 11 wherein —O-alkylene- is —O-methylene-.

15. The compound of claim 1 wherein R is arylene, X is —O-alkylene-O—, $R_1$ and $R_2$ are hydrogen and n is 0.

16. The compound of claim 15 wherein —O-alkylene-O— is —O-ethylene-O—.

17. The compound of claim 1 wherein R is arylene, X is —O-alkylene-ONH—, $R_1$ and $R_2$ are hydrogen and n is 0.

18. The compound of claim 17 wherein —O-alkylene-O-NH— is butyrolactamide.

19. The compound of claim 1 wherein R is arylene, X is —O-alkylene-OC(O)NH—, $R_1$ and $R_2$ are hydrogen and n is 0.

20. The compound of claim 19 wherein —O-alkylene-OC(O)NH— is —O-ethylene-OC(O)NH—.

* * * * *

UNITED STATES PATENT AND TRADEMARK OFFICE
CERTIFICATE OF CORRECTION

PATENT NO.   : 6,235,901 B1
DATED        : May 22, 2001
INVENTOR(S)  : Bill M. Culbertson et al.

It is certified that error appears in the above-identified patent and that said Letters Patent is hereby corrected as shown below:

Column 2,
Line 24, replace "Burkin" with -- Bufkin --.

Column 3,
Line 23, replace "O-alkyl-OHN,) or" with -- O-alkyl-ONH, or --.
Line 32, replace "polymerized or opolymerized," with -- polymerized or copolymerized, --.

Column 7,
Line 1, replace "Recrystallizion" with -- Recrystallization --.

Column 10,
Line 57, replace "FT-IR and is" with -- FT-IR and --.

Signed and Sealed this

Nineteenth Day of February, 2002

Attest:

Attesting Officer

JAMES E. ROGAN
Director of the United States Patent and Trademark Office